United States Patent

Bokerman et al.

Patent Number: 5,095,131
Date of Patent: Mar. 10, 1992

[54] METAL ASSISTED ALKYLATION OF SILICA

[75] Inventors: Gary N. Bokerman; John P. Cannady, both of Madison, Ind.; Douglas H. Lenz, Princeton, N.J.

[73] Assignee: Dow Corning Corporation, Midland, Mich.

[21] Appl. No.: 615,113

[22] Filed: Nov. 19, 1990

[51] Int. Cl.$^5$ ............................................. C07F 7/08
[52] U.S. Cl. .................................... 556/456; 556/453; 556/460; 556/467
[58] Field of Search ................. 556/467, 460, 452; 532/453

[56] References Cited

U.S. PATENT DOCUMENTS

| | | | |
|---|---|---|---|
| 2,914,549 | 11/1959 | Anderson | 260/448.2 |
| 2,961,453 | 11/1960 | Sleddon | 260/448.2 |
| 4,202,831 | 5/1980 | Schlah et al. | 556/467 |
| 4,417,067 | 11/1983 | Kötzsch et al. | 556/467 |
| 4,762,940 | 8/1988 | Halm et al. | 556/472 |
| 4,824,985 | 4/1989 | Goodwin et al. | 556/460 |

Primary Examiner—Paul F. Shaver

[57] ABSTRACT

The described invention is a process for producing silanes and polysiloxanes. The process comprises contacting silica with a preformed alkylaluminum compound in the presence of a catalyst effective in facilitating the reaction. Preferred catalysts are copper, tin, zinc, phosphorous, and compounds thereof.

15 Claims, No Drawings

METAL ASSISTED ALKYLATION OF SILICA

BACKGROUND OF THE INVENTION

The described invention is a process whereby a preformed alkylaluminum compound is reacted with silica, in the presence of a catalyst, to form silanes and polysiloxanes.

Halosilanes, alkylated silanes, and polysiloxanes species are important intermediates in the production of commercially useful organosilanes and organopolysiloxane products. Typically, the precursor silanes are formed by a direct process reaction of elemental silicon with an alkyl halide in the presence of a copper catalyst. The elemental silicon required for this direct process is usually produced by the carbothermic reduction of silicon dioxide in an electric-arc furnace. This is a high energy input process and thus makes the cost of elemental silicon an important cost in the production of organosilanes and organopolysiloxane products.

Considerable work has been reported on the use of catalysts and promoters to increase the conversion of silicon in the direct process as well as to increase selectivity of the direct process for more desirable species of product. Halm et. al. U.S. Pat. No. 4,762,940, issued Aug. 9, 1988, provides a useful summary of this work. In addition, Halm et al. extends the teaching of the prior art by describing combinations of copper, zinc, phosphorous, and arsenic or compounds thereof effective in modifying the efficiency and product distribution of the direct process. However, even with continued optimization of the direct process to reduce product cost, cost reduction is inherently limited by the high cost of elemental silicon. Therefore, a cost effective process which bypasses the need for elemental silicon is desirable.

A process for directly converting silica to organosilanes and organopolysiloxanes could offer cost saving advantages. Such processes have been reported.

Anderson, U.S. Pat. No. 2,914,549, issued Nov. 24, 1959, describes a process for the production of alkyl silanes or alkylhalosilanes comprising reacting together silica and an alkylaluminum halide. The described process was ran at elevated pressure and in a temperature range of 200° C. to 330° C. Anderson teaches the alkylaluminum halide may be formed in situ by reaction of an alkyl halide and aluminum and that this reaction may be initiated by the addition of copper.

Sleddon, U.S. Pat. No. 2,961,453, issued Nov. 22, 1960, describes a process for production of alkyl silanes comprising reacting together a siliceous material and alkali metal halide complexes of a organoaluminum halide having the general formula $MXRAlY_2$, where M is an alkali metal, R is a methyl or ethyl group and X and Y are halides. The useful alkali metals were reported to be sodium, potassium, lithium, and cesium.

In general, the process of reacting alkylaluminum halides with silica has not been found to be cost efficient in comparision to the the direct route. This inefficiency is primarily due to poor conversion of silicon and poor product selectivity. Therefore, it is a purpose of the instant invention to provide a process whereby certain catalysts are described which can increase silicon conversion and modify product selectivity.

SUMMARY OF THE INVENTION

The described invention is a process for producing silanes and polysiloxanes. The process comprises contacting silica with a preformed alkylaluminum compound in the presence of a catalyst effective in facilitating the reaction.

DESCRIPTION OF THE INVENTION

The presently described invention is a process for preparation of silanes of formula $$R_bSiX_{4-b},$$

polysiloxanes of formula $$R_cX_{2n+2-2c}Si_nO_{n-1},$$

and cyclic polysiloxanes of formula $$(R_dX_{2-d}SiO)_e;$$

where each R is an independently chosen alkyl radical of 1 to 6 carbon atoms, X is a halogen, b is an integer of 0 to 4, n is an integer from 2 to 6, c is an integer from 0 to 2n+2, d is an integer from 0 to 2, and e is an integer from 3 to 10.

The claimed process comprises: contacting silica with a preformed alkylaluminum compound of formula $$R_aAlX_{3-a};$$

where R and X are as previously described and a is 1, 2, or 3; in the presence of a catalyst; at a temperature in a range of 100° C. to 350° C.

The product silanes, polysiloxanes, and cyclic polysiloxanes of the instant described process may be substituted with halogen atoms, alkyl radicals of one to six carbon atoms, or combinations thereof. The halogen atom, X, can be bromide, chloride, fluoride, and iodide. The preferred halogen atom is chloride. The alkyl radical, R, can consist of one to six carbon atoms arranged in a straight or branched chain configuration. The alkyl radical can be, for example, methyl, ethyl, propyl, isopropyl, n-butyl, isobutyl, tert-butyl, sec-butyl, pentyl, or hexyl. Methyl is the preferred alkyl radical.

Silanes which may be produced by the described processes include, for example, tetrachlorosilane, methyltrichlorosilane, dimethyldichlorosilane, trimethylchlorosilane, tetramethylsilane, ethyltrimethylsilane, ethyltrichlorosilane, diethyldichlorosilane, isobutyltrichlorosilane, hexyltrichlorosilane, methyltribromosilane, dimethyldibromosilane, methylfluorosilane, dimethyldifluorosilane, methyltriiodosilane, methyltrifluorosilane, and dimethyldifluorosilane.

Polysiloxanes that may be produced by the described process include, for example, hexamethyldisiloxane, hexaethyldisiloxane, pentamethylchlorodisiloxane, and octamethyltrisiloxane.

Cyclic polysiloxanes that may be produced by the described process include, for example, hexamethylcyclotrisiloxane, octamethylcyclotetrasiloxane, decamethylcyclopentasiloxane, heptamethylchlorocyclotetrasiloxane, hexaethylcyclotrisiloxane, and octaethylcyclotetrasiloxane.

The silica employed in the instant described process is silicon dioxide, $SiO_2$, in its many forms. The silica includes crystalline forms of $SiO_2$ as well as amorphous types, for example, silica gel, fumed silica, and precipitated silica. Preferred are amorphorous silicas, as they are normally more reactive than crystalline silica. Reactivity of the silica tends to increase with the available surface area. Therefore, the smaller the particle size the more reactive the silica. Preferred, is silica with an average particle size less than about 100 μm in in diameter. Even more preferred is silica with an average particle size less than about 2 μm in diameter. The lower limit for particle size is limited only by the ability to produce and handle. Silica with particle sizes greater than about 100 μm may work in the process, but reactivity may be reduced.

The silica is contacted with a preformed alkylaluminum compound of formula $R_aAlX_{3-a}$, where R is an alkyl and X is a halogen as previously described. The value of a can be 1, 2, or 3. By "preformed" it is meant the alkylaluminum compound is formed separate from the instantly described process and subsequently combined with the silica and catalyst as a distinct comound. The alkylaluminum compound is not formed in situ in the instant described process. The alkylaluminum compound can be, for example, methylaluminum dichloride, methylaluminum sesquichloride, dimethylaluminum chloride, dimethylaluminum iodide, ethylaluminum sesquichloride, ethylaluminum sesquibromide, ethylaluminum sesquiiodide, ethylaluminum dichloride, trimethylaluminum, diethylaluminum chloride, tripropylaluminum, tributylaluminum, diisobutylaluminum chloride, dipropylaluminum chloride, and diisoamylaluminum chloride.

The silica and alkylaluminum compound are contacted in the presence of a catalyst effective in facilitating reaction of the silica with the alkylaluminum compound. By effective, it is meant materials, typically metals and compounds thereof, which increase the conversion of silica to silanes and siloxanes, increase the rate of conversion of silica to silane and siloxane products, or modify the distribution of silane and siloxane products.

Materials which are effective catalysts in the described process are metal and metal compounds selected from the group consisting of: copper and copper compounds, tin and tin compounds, zinc and zinc compounds, antimony and antimony compounds, mercury and mercury compounds, iron and inorganic iron compounds, manganese and manganese compounds, nickel and nickel compounds, phosphorous, metal phosphides, metal phosphorous alloys, and mixtures and alloys thereof.

Preferred, are catalysts selected from the group consisting of copper and copper compounds, tin and tin compounds, zinc and zinc compounds, phosphorous and phosphorous compounds, and mixtures and alloys thereof.

The optimal concentration of the catalyst will depend on both the type of catalyst used as well as the the product distribution desired. Representative catalyst concentrations can be found in the provided examples. In general, concentrations of catalyst above about 300 ppm, in relation to the weight of silica, have been shown to be effective in increasing converison of silica to silane and siloxane products. Concentrations of catalysts greater than about 80 ppm, in relation to the silica, have been shown to be effective in modifying product distributions. Preferred are effective concentrations of catalyst less than about one weight percent of the combined catalyst and silica weight. No additional benefit is perceived for concentrations of catalyst above about ten weight percent of the combined catalyst and silica weight.

The catalyst can be in any convenient particulate form, such as powder, granule, flake, or chip.

The silica, alkylaluminum compound, and catalyst are contacted at a temperature in a range of about 100° C. to 350° C. A preferred temperature range is about 275° C. to 325° C.

The silica, catalyst, and alkylaluminum compound are contacted by standard means. The means for contacting the mixture of silica and catalyst with the alkylaluminum compound can be a batch or continuous process. The contact means can be, for example, a fixed-bed reactor, a stirred-bed reactor, a vibrating-bed reactor or a fluidized-bed reactor.

The reaction is preferably carried out by heating the reactants together under pressure, which may be the autogenous pressure generated at the temperature of reaction. The reaction may, however, also be carried out under atmospheric or subatmospheric pressures. Normally the reaction proceeds more quickly at higher pressures. It is preferred that the reaction be conducted in an environment essentially free of water and oxygen, this may be achieved by standard means, for example, a vaccum or purging with an inert gas.

The time required for products to be formed will depend on the reactivity of the silica used, the temperature, the alkylaluminum compound, and the catalyst. Normally, times in the range of about two to ten hours are sufficient.

The ratio of aluminum atoms to silica atoms is not critical to the presently described process. However, a preferred ratio of aluminum atoms to silicon atoms is in the range of 1.0 to 3.0.

The following examples are offered as illustrative of the instant invention. These examples are not to be construed as limiting on the claimed invention.

All of the reported runs were conducted in a pressurized Parr 300 cc mini-reactor. The reactor was connected at the inlet, outlet, and sampling ports to an inert vaccum manifold system. The manifold system allowed all parts of the reaction system to be maintained essentially air and moisture free. Typically, the reactor and associated lines, traps, and sample cylinders were heated for three to five hours in flowing nitrogen to remove traces of air and water. The silica and catalysts were added to the reactor and the temperature brought to the desired level. Methylaluminum sesquichloride was then added to the reactor. The reactor was allowed to proceed for two to three hours, with constant stirring, and with periodic sampling of product gases.

Gases for product sampling were first drawn through a 100° C. trap to remove methylaluminum sesquichloride and/or $AlCl_3$ and then collected in a cylinder packed in dry ice. The product components of the sampled gases were determined by gas chromotography and gas chromotography/mass spectrometry.

EXAMPLE 1

A group of runs were made where the reactor was brought to a fixed temperature prior to addition of the methylaluminum sesquichloride and maintained at that temperature throughout the run. The results of these runs are presented in Table 1. Table 1 presents the effect of temperature (°C.), the molar ratio of aluminum to silicon (Al/Si Ratio), the effects of metal concentrations (ppm metal) as catalyst on conversion of silicon (% Si Conv.), and product selectivity. The ppm metals is expressed in relation to total silica and metals present in the charge to the reactor. The conversion of silicon is expressed as the percent of initial silicon added as silica to the reactor. Conversion of silicon was determined by the amount of unreacted silica remaining in the reactor. The term "Product selectivity" refers to the mole percent each listed species represents of the total trapped product gas. The silica was fumed silica FK310 (Degussa, Tetersboro, N.J.). The methylaluminum sesquichloride was purchased from Texas Alkyls, Houston, Tex. The copper was in the form of copper (I) chloride and copper metal powders. Zinc was added in the form of a zinc chloride powder. Phosphorous was added in the form of a phosphorous-copper alloy powder. Tin was added in the form of anhydrous tin (II) chloride powder. The results are presented in Table 1.

EXAMPLE 2

In this series of runs the reactor temperature was at 25° C. when the methylaluminum sesquichloride was added to the reactor. The reactor temperature was then raised to 300° C. This procedure is referred to as a variable temperature process. The results are presented in Table 2. The headings for Table 2 are as described for Table 1. Also, presented in Table 2 is the rate of silicon conversion to products (Moles si/hr). The silica was fumed silica with a particle size of 100 μm and surface area of 450 m²/g (Degussa, Tetersboro, N.J.). Other compounds and metals were as described for Example 1.

TABLE 1

Reaction of Silica and Methylaluminum Sesquichloride, Under Fixed Temperature Conditions, in The Presence of Metal Catalysts.

| | Run No. | | | | | |
|---|---|---|---|---|---|---|
| | 18 | 12 | 13 | 10 | 11 | 22 |
| Temp. (°C.) | 300 | 300 | 300 | 300 | 200 | 115 |
| Press (psia) | 30 | 115 | 95 | 115 | 60 | 30 |
| Al/Si Ratio | 1.3 | 1.7 | 1.7 | 1.7 | 1.1 | 1.3 |
| % Si Conv. | 15 | 8 | 23 | 20 | 4 | 4 |
| Metals (ppm) | | | | | | |
| P | 147 | 179 | 1221 | 747 | 683 | 147 |
| Sn | 29 | 83 | 687 | 763 | 207 | 200 |
| Cu | 103 | 1513 | 142883 | 87180 | 117945 | 588 |
| Zn | 73 | 633 | 2671 | 2242 | 2690 | 1136 |
| Product Selectivity | | | | | | |
| $Me_4Si$ | 28.3 | 0.0 | 1.7 | 9.5 | 18.5 | 96.6 |
| $Me_3SiCl$ | 0.0 | 87.1 | 55.8 | 2.4 | 0.0 | 0.0 |
| $EtMe_3Si$ | 0.0 | 0.0 | 0.0 | 0.0 | 0.0 | 0.0 |
| $Me_2SiCl_2$ | 0.0 | 0.5 | 39.4 | 0.0 | 0.0 | 0.0 |
| $Me_6Si_2O$ | 65.8 | 10.6 | 2.5 | 81.6 | 81.5 | 3.4 |
| $Me_5ClSi_2O$ | 5.9 | 1.5 | 0.6 | 6.4 | 0.0 | 0.0 |
| $Me_8Si_3O_2$ | 0.0 | 0.3 | 0.1 | 0.2 | 0.0 | 0.0 |

TABLE 2

Reaction of Silica and Methylaluminum Sesquichloride, Under Variable Temperature Conditions, in The Presence of Metal Catalysts.

| | Run No. | | | | |
|---|---|---|---|---|---|
| | 19 | 5 | 6 | 7 | 20 |
| Temp. (°C.) | 300 | 300 | 300 | 300 | 300 |
| Press (psia) | 225 | 95 | 280 | 260 | 200 |
| Al/Si Ratio | 1.4 | 0.7 | 1.5 | 1.6 | 1.3 |
| % Si Conv. | 40 | 24 | 64 | 50 | 54 |
| Mole Si/hr | 0.06 | 0.02 | 0.19 | 0.08 | 0.08 |
| Metals (ppm) | | | | | |
| P | 353 | 333 | 240 | 717 | 387 |
| Sn | 22 | 299 | 320 | 384 | 409 |
| Cu | 573 | 75984 | 98753 | 179337 | 3396 |
| Zn | 154 | 2028 | 3256 | 5124 | 1902 |
| Product Selectivity | | | | | |
| $Me_4Si$ | 32.1 | 2.2 | 0.7 | 2.3 | 11.3 |
| $Me_3SiCl$ | 62.1 | 85.4 | 59.7 | 79.2 | 86.1 |
| $EtMe_3Si$ | 0.0 | 0.0 | 0.0 | 0.0 | 0.0 |
| $Me_2SiCl_2$ | 1.7 | 0.1 | 37.6 | 12.1 | 0.2 |
| $Me_6Si_2O$ | 3.6 | 11.8 | 1.1 | 5.1 | 2.4 |
| $Me_5ClSi_2O$ | 0.4 | 0.5 | 0.8 | 1.3 | 0.0 |
| $Me_8Si_3O_2$ | 0.0 | 0.1 | 0.2 | 0.1 | 0.0 |

Run 18 is considered a baseline run against which other runs in this series are compared. To evaluate the effect of metals as catalyst, additional metals were added in the other reported runs. The data presented in Table 1 demonstrate that increases in copper, tin, zinc, and phosphorous are correlated with changes in the silicon product distribution. The data in Table 1 also demonstrate the effect of temperature on silicon conversion.

Run 19 is considered a baseline run against which other runs in this series are compared. To evaluate the effect of metals as catalyst, additional metals were added in the other reported studies. It can be seen, from the data presented in Table 2, that increasing the Al/Si molar ratio increases the percent silicon conversion significantly. Changes in the Al/Si molar ratio have little effect on product selectivity. The data presented in Table 2 demonstrate that the addition of copper, tin, and zinc to the process results in increase conversion of silica to products. The data presented in Table 2 also suggest that the variable temperature process may result in higher conversions of silicon that when the process is run as a fixed temperature process.

EXAMPLE 3

The effects of silica type, particle size, and surface area were evaluated. The process was ran at a fixed reactor temperature of 300° C., with the exception of run 9, which was ran under variable temperature conditions as previously described. The type silicas tested were silica gel, W. R. Grace (Baltimore, Md.); fumed silica, North America Silica Co. (Tetersboro, N.J.); and silica quartz, Bond Ottawa silica (Ottawa, Ill.). The particle size in micrometers ($\mu$m) and surface area in meters squared per gram ($m^2/g$) are presented in Table 3. Other headings are as previously described for Table 2. Other materials are as described in Example 1.

TABLE 3

Effect of Silica Type, Particle Size, and Surface Area on The Reaction With Methylaluminum Sesquichloride, in The Presence of Metal Catalysts.

| | Run No. | | | | |
|---|---|---|---|---|---|
| | 1 | 3 | 6 | 9 | 8 |
| Silica Type | Gel | Fumed | Fumed | Fumed | Quartz |
| Particle Size ($\mu$m) | >100 | 5 | 100 | 2 | >100 |
| Surface Area ($m^2/g$) | 450 | 650 | 190 | 180 | 11 |
| Press (psia) | 210 | 70 | 280 | 65 | 245 |
| Al/Si Ratio | 48 | 30 | 1.5 | 2.8 | 1.5 |
| % Si Conv. | — | 42 | 64 | 10 | 10 |
| Mole Si/hr | 0.13 | 0.06 | 0.09 | 0.03 | 0.01 |
| Metals (ppm) | | | | | |
| P | 489 | 537 | 240 | 861 | 529 |
| Sn | 339 | 442 | 320 | 396 | 109 |
| Cu | 34610 | 93714 | 98753 | 96986 | 73726 |
| Zn | 556 | 2320 | 3256 | 1708 | 2335 |
| Product Distribution | | | | | |
| $Me_4Si$ | 15.7 | 0.0 | 0.7 | 0.9 | 95.0 |
| $Me_3SiCl$ | 59.1 | 99.1 | 59.7 | 8.4 | 0.0 |
| $EtMe_3Si$ | 0.0 | 0.0 | 0.0 | 0.0 | 0.2 |
| $Me_2SiCl_2$ | 10.6 | 1.0 | 37.6 | 89.4 | 4.7 |
| $Me_6Si_2O$ | 13.6 | 0.0 | 1.1 | 1.1 | 0.1 |
| $Me_5ClSi_2O$ | 1.0 | 0.0 | 0.8 | 0.3 | 0.0 |
| $Me_8Si_3O_2$ | 0.0 | 0.0 | 0.2 | 0.0 | 0.0 |

The data presented in Table 3 demonstrate that the product distributions achieved with silica gel and fumed silica are similar. Quartz is less reactive in all cases, with selectivity principally for tetramethylsilane.

The data presented in Table 3 also demonstrate that available surface area has an effect on conversion of silica to products and on the distribution of these products.

What is claimed is:

1. A process for preparation of silanes of formula $$R_bSiX_{4-b},$$

polysiloxanes of formula $$R_cX_{2n+2-c}Si_nO_{n-1},$$

and cyclic polysiloxanes of formula $$(R_dX_{2-d}SiO)_e;$$

where each R is an independently chosen alkyl radical of 1 to 6 carbon atoms, X is a halogen, b is an integer of 0 to 4, n is an integer from 2 to 6, c is an integer from 0 to 2n+2, d is an integer from 0 to 2, and e is an integer from 3 to 10; the process comprising:

contacting silica with a preformed alkylaluminum compound of formula $$R_aAlX_{3-a};$$

where R and X are as previously described and a is 1, 2, or 3; in the presence of a catalyst effective in facilitating the reaction between the silica and the preformed alkylaluminum compound; at a temperature within a range of 100° C. to 350° C.

2. A process according to claim 1, where the catalyst is selected from a group consisting of copper and copper compounds, tin and tin compouhnds, zinc and zinc compounds, antimony and antimony compounds, mercury and mercury compounds, iron and inorganic iron compounds, manganese and manganase compounds, nickel and nickel compounds, phosphorous, metal phosphides, metal phosphorous alloys, and mixtures and alloys thereof.

3. A process according to claim 2, where the catalyst is selected from a group consisting of copper and copper compounds, tin and tin compounds, zinc and zinc compounds, phosphorous and phosphorus compounds, and mixture and alloys thereof.

4. A process according to claim 3, where the temperature is within a range of 275° C. to 325° C.

5. A process according to claim 4, where the alkyl radical is selected from a group consisting of methyl and ethyl radicals.

6. A process according to claim 5, where the halogen is chloride.

7. A process according to claim 6, where the alkylaluminum compound is methylaluminum sesquichloride.

8. A process according to claim 7, where the silica is selected from a group consisting of silica gel, fumed silica, and precipitated silica.

9. A process according to claim 8, where the silanes comprise tetramethylsilane.

10. A process according to claim 8, where the silanes comprise trimethylchlorosilane.

11. A process according to claim 8, where the silanes comprise dimethyldichlorosilane.

12. A process according to claim 8, where the polysiloxanes comprise hexamethyldisiloxane.

13. A process according to claim 8, where the polysiloxanes comprise pentamethylchlorodisiloxane.

14. A process according to claim 8, where the polysiloxanes comprise octamethyltrisiloxane.

15. A process according to claim 1, where the catalyst is selected from a group consisting of copper and copper compounds.

* * * * *